United States Patent [19]

Aoki et al.

[11] Patent Number: 5,609,882
[45] Date of Patent: Mar. 11, 1997

[54] ETOPOSIDE PREPARATIONS

[75] Inventors: Minoru Aoki, Tokyo; Minoru Nakada, Kitamoto; Yuichi Yazawa, Tokyo; Gen'ichi Izu, Saitama-ken; Takashi Terada, Konosu, all of Japan

[73] Assignee: Nippon Kayaku Kabushiki Kaisha, Tokyo, Japan

[21] Appl. No.: 402,778

[22] Filed: Mar. 9, 1995

Related U.S. Application Data

[63] Continuation of Ser. No. 90,909, Jul. 13, 1993, abandoned, which is a continuation of Ser. No. 857,730, Mar. 26, 1992, abandoned, which is a continuation of Ser. No. 530,881, May 30, 1990, abandoned.

[30] Foreign Application Priority Data

Jun. 7, 1989 [JP] Japan .................................. 1-142983

[51] Int. Cl.$^6$ ....................................... A61K 9/48
[52] U.S. Cl. .......................... 424/451; 424/455; 424/456; 424/457; 514/25; 514/27; 514/33; 514/962
[58] Field of Search ..................................... 424/451, 455, 424/456, 457; 514/25, 27, 33, 962

[56] References Cited

U.S. PATENT DOCUMENTS

| | | | |
|---|---|---|---|
| 4,701,327 | 10/1987 | Henmi et al. | 424/455 |
| 4,734,284 | 3/1988 | Terada et al. | 424/455 |
| 4,772,589 | 9/1988 | Kaplan et al.1 | 514/33 |

OTHER PUBLICATIONS

CA 105(18):158871f.

*Primary Examiner*—Raj Bawa
*Attorney, Agent, or Firm*—Nields & Lemack

[57] ABSTRACT

This invention relates to an etoposide preparation containing an etoposide composition comprising an etoposide, polyvinylpyrrolidone, and water-soluble cellulose ether derivative wherein the proportion of the respective components is about 0.25 to 2 parts by weight for polyvinylpyrrolidone and about 0.0028 to 0.2 parts by weight for the water-soluble cellulose ether derivative per 1 part by weight of the etoposide, and about 10 to 20% (w/w) for the etoposide in the whole amount of the composition.

10 Claims, No Drawings

ETOPOSIDE PREPARATIONS

This application is a continuation of application Ser. No. 08/090,909 filed Jul. 13, 1993 (abandoned), which is a continuation of application Ser. No. 07/857,730 filed Mar. 26, 1992 (abandoned), which is a continuation of application Ser. No. 07/530,881 filed May 30, 1990 (abandoned).

BACKGROUND OF THE INVENTION

1. Field of the Invention

The present invention relates to pharmaceutical preparations of etoposide, i.e. 4'-demethylepipodophillotoxin-9-(4, 6-O-ethylidene-β-D-glucopyranoside), which is being put on the market as an antitumoral agent.

2. Description of the Prior Art

There is already known an etoposide preparation comprising an etoposide solution composition containing etoposide and a water-soluble cellulose ether derivative or polyvinylpyrrolidone (U.S. Pat. No. 4734284). Said preparation has been designed to show a reduced tendency to separate out crystals of etoposide, difficultly soluble in water, when added into water and an improved absorbability in a living body.

According to the Examples given in said U.S. Patent specification, however, the content of etoposide in the preparation is only 5–8%. Consequently it presents, when intended for use as encapsulated preparations, a problem of excessively large capsule size. Since etoposide is difficultly soluble in water, it has been very difficult to increase the etoposide content in its solution from the viewpoint of suppressing the separating out of its crystals which might occur when the solution is added into water.

Further, prior preparations show decrease in the etoposide content with lapse of time when tested under severe conditions, so that development of an etoposide preparation having enhanced stability for the lapse of time has been eagerly desired.

SUMMARY OF THE INVENTION

Under the circumstances, the present inventors have made an extensive study and, as the result, found that an etoposide solution composition containing (1) etoposide and (2) polyvinylpyrrolidone and a water-soluble cellulose ether derivative shows a reduced tendency to separate out its crystals when added into water even at a concentration of as high as 10% or more and an improved stability for the lapse of time. The present invention has been accomplished based on the above finding.

According to the present invention, there is provided an etoposide preparation comprising an etoposide solution composition containing etoposide, a water-soluble cellulose ether derivative and polyvinylpyrrolidone.

DETAILED DESCRIPTION OF THE INVENTION

The present invention will be described in more detail below.

The solvents to be used for dissolving etoposide in the present invention are not particularly limited so long as they are capable of dissolving etoposide, are pharmacologically acceptable, and are liquid or semisolid at ordinary temperatures, but usually alcohols are used. Examples of the alcohol include lower alkyl alcohols such as ethanol; glycerol; and low molecular or high molecular glycols, such as propylene glycol and polyethylene glycols 300, 400 and 600. Preferably used among alcohols are glycols. Particularly preferred from the viewpoint of suppressing the precipitation of crystals of etoposide, which is difficultly soluble in water, are polyalkylene glycols, particularly polyethylene glycols having an average molecular weight of 300–1,000, preferably 400–800, more preferably 600. These solvents may be used each alone or in mixtures of two or more. The solvents are used in an amount of generally 4 to 10, preferably 4.5 to 7, parts by weight for 1 part by weight of etoposide.

As examples of water-soluble cellulose ether derivatives advantageously used in the present invention, mention may be made of water-soluble cellulose derivatives having a structure resulting from substitution of the hydroxyl groups of cellulose with a hydroxyalkoxy group and/or a lower alkoxy group, such as hydroxypropylcellulose, hydroxypropylmethylcellulose and methylcellulose. The viscosity (2% aqueous solution at 20° C.) of the cellulose ethers is 8000 cps or less, preferably about 2–1500 cps, more preferably about 3–500 cps.

The molecular weight of polyvinylpyrrolidone is subjected to no special restriction. Both said polymer of an average molecular weight of 40,000 and that of the molecular weight of 700,000 can be used without discrimination. However, those favorably used have an average molecular weight of about 10,000–1,200,000, preferably about 20,000–50,000, more preferably about 20,000–30,000. As to the amount used of these additives per 1 part by weight of etoposide, it is about 0.25–2, preferably about 0.5–1.5, more preferably about 0.5–1, part by weight for polyvinylpyrrolidone, and about 0.0028–0.2, preferably about 0.01–0.1, more preferably about 0.02–0.08, part by weight for water-soluble cellulose ether derivatives.

As to the amount used of polyvinylpyrolydone and solvent per 1 part by weight of water-soluble cellulose ether derivatives, it is about 5 to 70, preferably about 10 to 60, more preferably about 10 to 50, parts by weight for polyvinylpyrrolidone, and about 70–300, preferably about 75–300, parts by weight for the solvent.

The pharmaceutical preparations of the present invention may be obtained by dissolving etoposide in a solvent, then adding said additives to the solution and filling the resulting solution composition into a containers such as gelatin capsules. It is preferable to fill the solution composition in hard gelatin capsule shells at room temperature (15° C.) to 60° C. by means of liquid filling to obtain an encapsulated preparation, or to prepare soft gelatin capsules by the plate process or by means of a capsule filler of the rotary die type.

In making the present preparations, it is useful for the stabilization of etoposide to add to the etoposide solution composition about 0–0.2 part by weight, preferably about 0.01–0.1 part by weight, of an organic acid such as citric acid, tartaric acid, malic acid, succinic acid, and fumaric acid relative to 1 part by weight of etoposide.

Other additives such as stabilizers, flavoring agents, and aromatizing agents may also be added to the solution composition.

As to the proportion of the respective components of the solution composition contained in the present preparation, it is about 9–25%, preferably about 10–20%, more preferably about 11–15% for etoposide; about 5–20%, preferably about 5–15%, more preferably about 6–14% for polyvinylpyrrolidone; about 0.01–5%, preferably about 0.05–2%, more preferably about 0.2–1% for water-soluble cellulose ether derivative; about 60–80%, preferably about 65–80% for solvent; and 0 to about 5%, preferably about 0.2–3%, more preferably about 0.4–1% for organic acid. The symbol "%" is % weight by weight "% (w/w)".

The effect of the present invention will be demonstrated below with reference to Experimental Examples.

In the Experimental Examples, the polyvinylpyrrolidone used was K-30 (average molecular weight: about 40,000) or K-25 (average molecular weight: about 25,000) and the hydroxypropylcellulose used was HPC-SL (viscosity: 3.5–5.9 cps). The "parts" are parts by weight.

EXPERIMENTAL EXAMPLE 1

Experiment on precipitation of crystals

A dissolution tester described in Pharmacopeia of Japan, 10th Ed. was used. The testing liquid used was distilled water (250 ml) at 37° C. Agitation was conducted by using a paddle stirrer at 200 r.p.m.

Thus, 3.2 g of a sample solution (etoposide content: 13.8%) according to the present invention prepared by dissolving 100 parts of etoposide, 50 parts of polyvinylpyrrolidone (K-30) and 4 parts of hydroxypropylcellulose in 570 parts of polyethylene glycol 400 was poured into the testing liquid, and the situation of precipitation of crystals after 30 minutes was observed. Resultantly, no precipitation of crystals was recognized.

EXPERIMENTAL EXAMPLE 2

Test for drug concentration in blood
1. Sample

Sample of the present invention (1): This was prepared by dissolving 1 part of etoposide, 0.8 part of polyvinylpyrrolidone (K-25), 0.04 part of hydroxypropylcellulose and 0.05 part of citric acid in 6.00 parts of polyethylene glycol 600 and filling the resulting solution in soft gelatin capsule shells.

Control sample: This was prepared by dissolving 1 part of etoposide, 0.04 part of hydroxypropylcellulose and 0.05 part of citric acid in 12 parts of polyethylene glycol 400 and filling the resulting solution in soft gelatin capsule shells.
2. Testing method Each sample was administered to a male beagle dog and the etoposide concentration in blood was determined over a period of 360 minutes. From the curve of etoposide concentration in blood thus determined, the total concentration of etoposide over a period of 360 minutes was determined and the ratio of said concentration to that determined for control was calculated by taking the latter as 100.
3. Results of experiment The results obtained are shown in the following Table.

| Sample | Ratio of concentration in blood |
| --- | --- |
| Control | 100 |
| Sample of the present invention | 98 |

As is apparent from the Table, the solution preparation of the present invention showed about the same ratio of etoposide concentration in blood as that shown by the control preparation and thus showed an equally good absorbability in living body to that of the control.

EXPERIMENTAL EXAMPLE 3

Stability test
1. Sample

The sample of the present invention of Experimental Example 2 was taken as the sample of the present invention (1), and a sample having the same composition as above except that citric acid had been eliminated therefrom was taken as the sample of the present invention (2). The control sample of Experimental Example 2 was taken as the control.
2. Testing method Each sample was stored at 80° C. for 3 days and the etoposide content in the sample preparation was determined by liquid chromatography, from which the remaining rate of etoposide was calculated.
3. Results of experiment The results obtained are shown in the following Table.

| Sample | Remaining rate of etoposide (3 days at 80° C.) |
| --- | --- |
| Sample of the present invention (1) | 99.5% |
| Sample of the present invention (2) | 91.8% |
| Control sample | 76.8% |

As is apparent from the Table, the. remaining rate of etoposide in the control sample is only 76.8% even though it contains citric acid. On the other hand, the rate in the sample of the present invention (1), which contains citric acid, is as high as 99.5% and essentially no decrease in etoposide content is recognized. Even the sample of the present invention (2), which contains no citric acid, shows a high value of said rate of 91.8%. These results reveal the highly excellent storage stability of the preparation of the present invention. Further, the sample of the present invention (3) was prepared by filling in a hard gelatin capsule an etoposide solution used in the sample of the present invention (1) of Experimental Example 2. The sample (3) was preserved at 80° C. for 10 days. As the results, the remaining rate of etoposide was 100%, which indicated no decrease of etoposide content.

As is apparent from the foregoing, according to the present invention, the separating out of etoposide crystals which would occur when an etoposide solution is added into water can be sufficiently suppressed even in a high concentration solution of an etoposide content of 10% or more, and also no lowering in absorbability in living body is recognized. Consequently, the size of the encapsulated preparation of the present invention can be reduced to ⅔ to ½ that of the capsule described in said U.S. Pat. No. 4,734,284. Further, the preparation of the present invention shows an excellent stability for the lapse of time even under severe conditions. Particularly, the preparations filled in a hard capsule show no decrease of etoposide content, and are very low in deterioration. This means that the preparations filled in a hard gelatin capsule are practically excellent.

Thus, according to the present invention, it has become possible to obtain an etoposide preparation which shows good stability for the lapse of time and good absorbability in a living body and is small in size and easy to administer orally.

The present invention is illustrated in detail below with reference to Examples, in which "parts" are parts by weight.

EXAMPLE 1

Into 306 parts of polyethylene glycol 600 was dissolved 50 parts of etoposide followed by 40 parts of polyvinylpyrrolidone (K-25) and 4 parts of hydroxypropylcellulose (HPC-SL), to obtain a filling solution. Capsules each containing 50 mg of etoposide were prepared by filling 400 mg each of the filling solution in No. 2 hard gelatin capsule shells at 40°–50° C. by means of a capsule filling apparatus provided with a liquid filling unit.

EXAMPLE 2

A filling solution was prepared by dissolving 100 parts of etoposide in 520 parts of polyethylene glycol 400 and then dissolving 100 parts of polyvinylpyrrolidone (K-15, average molecular weight: 12,000) and 4 parts of hydroxypropylcellulose (HPC-SL, viscosity of 2% aq. solution at 20° C.: 6–10 cps) in the resulting solution. Soft capsules each containing 100 mg of etoposide were prepared by filling 724 mg each of the filling solution in soft gelatin capsule shells by means of a rotary die process machine and drying the filled capsules.

EXAMPLE 3

A filling solution was prepared by dissolving 100 parts of etoposide in 560 parts of polyethylene glycol 600 and then dissolving 60 parts of polyvinylpyrrolidone (K-90, average molecular weight: about 1,200,000) and 4 parts of methylcellulose in the resulting solution. Soft capsules each containing 100 mg of etoposide were obtained by filling 724 mg of the filling solution in each gelatin capsule by the plate process and drying the filled capsules.

EXAMPLE 4

A filling solution was prepared by dissolving 100 parts of etoposide in 466 parts of polyethylene glycol 400 and further dissolving 80 parts of polyvinylpyrrolidone (K-30), 5 parts of citric acid, 40 parts of glycerol and 4 parts of hydroxypropylmethylcellulose in the resulting solution. Soft capsules were obtained by filling 695 mg each of the filling solution in soft gelatin capsule shells by means of a rotary die process machine and drying the filled capsules.

EXAMPLE 5

Into 560 parts of polyethylene glycol 600 was dissolved 100 parts of etoposide followed by 100 parts of polyvinylpyrrolidone (K-25) and 2 parts of hydroxypropylmethylcellulose, to obtain a filling solution. Capsules each containing 100 mg of etoposide were prepared by filling 762 mg each of the filling solution in No. 0 hard gelatin capsule shells in the same manner as in Example 1.

EXAMPLE 6

Into 300 parts of polyethylene glycol 600 was dissolved 50 parts of etoposide followed by 30 parts of polyvinylpyrrolidone (K-25), 3 parts of citric acid and 1 part of hydroxypropylcellulose (HPC-SL). Capsules each containing 50 mg of etoposide were obtained by filling 384 mg each of the solution obtained above in No. 2 hard gelatin capsule shells in the same manner as in Example 1.

What is claimed is:

1. An etoposide preparation containing an etoposide solution consisting essentially of an etoposide, poiyvinylpyrrolidone, and water-soluble cellulose ether derivative having a structure resulting from substitution of the hydroxyl groups with hydroxyalkoxy and/or lower alkoxy groups and a viscosity of 8000 cps or less in a 2% aqueous solution at 20° C. wherein the amount of said etoposide present in said solution is 9–25% (w/w), the amount of said polyvinylpyrrolidone present in said solution is 5–20% (w/w), the amount of said cellulose ether derivative present in said solution is 0.01–5% (w/w), and the amount of organic acid present in said solution is 0–5% (w/w).

2. An etoposide preparation according to claim 1, wherein the proportion of polyvinylpyrrolidone is about 5 to 70 parts by weight per 1 part by weight of water-soluble cellulose ether derivative.

3. An etoposide preparation according to claim 2, wherein the water-soluble cellulose ether derivative is hydroxypropylcellulose.

4. An etoposide preparation consisting essentially of a capsule shell and, enclosed therein, an etoposide solution containing 11 to 15% w/w of etoposide, 5 to 20% w/w polyvinylpyrrolidone, 0.05 to 2% w/w water-soluble cellulose ether derivative having a structure resulting from substitution of the hydroxyl groups with hydroxyalkoxy and/or lower alkoxy groups and a viscosity of 8000 cps or less in a 2% aqueous solution at 20° C, and 60 to 80% w/w of polyethylene glycol.

5. An etoposide preparation according to claim 4, wherein the proportion of respective components relative to 1 part by weight of etoposide is about 0.5 to 1.5 part by weight for polyvinylpyrrolidone, about 0.01 to 0.1 part by weight for water-soluble cellulose ether derivative, and about 4.5 to 7 parts by weight for polyethylene glycol.

6. An etoposide preparation according to claim 5, wherein the polyvinylpyrrolidone is about 10 to 60 parts by weight and the polyethylene glycol is about 70 to 300 parts by weight per 1 part by weight of the water-soluble cellulose ether derivative.

7. An etoposide preparation according to claim 6, wherein the water-soluble cellulose ether derivative is hydroxypropylcellulose.

8. An etoposide preparation according to claim 6, wherein the water-soluble cellulose ether derivative is hydroxypropylcellulose having a viscosity (2% aqueous solution at 20° C.) of about 3 to 500 cps, the polyvinylpyrrolidone is polyvinylpyrrolidone having an average molecule weight of about 20,000 to 50,000, and the polyethylene glycol is polyethylene glycol having an average molecular weight of about 300 to 1,000.

9. An etoposide preparation consisting essentially of a gelatin capsule shell and, enclosed therein, an etoposide solution containing 11 to 15% w/w (w/w) of an etoposide, 6 to 14% w/w of polyvinylpyrrolidone having an average molecular weight of 20,000 to 50,000, 0.2 to 1% w/w of hydroxypropylcellulose having a viscosity (2% aqueous solution at 20° C.) of 3 to 500 cps, 65 to 80% w/w of polyethylene glycol having an average molecular weight of 400 to 800, and 0 to 5% w/w of an organic acid; the proportion of respective components relative to 1 part by weight of the etoposide being 0.5 to 1 part by weight for polyvinylpyrrolidone, 0.02 to 0.08 part by weight for hydroxypropylcellulose and 4.5 to 6 parts by weight for polyethylene glycol; and relative to 1 part by weight of hydroxypropylcellulose being 10 to 50 parts by weight for polyvinylpyrrolidone and 75 to 300 parts by weight for polyethylene glycol.

10. An etoposide preparation according to claim 9, wherein the gelatin capsule is a hard capsule.

* * * * *